(12) United States Patent
Weber et al.

(10) Patent No.: US 8,168,390 B2
(45) Date of Patent: May 1, 2012

(54) METHOD AND APPARATUS FOR DIAGNOSING AGE-RELATED MACULAR DEGENERATION

(75) Inventors: Bernhard H. F. Weber, Obertraubling (DE); Thomas Loenhardt, Regensburg (DE); Andrea Milenkovic, Köfering (DE); Lars G. Fritsche, Regensburg (DE)

(73) Assignee: University of Regensburg, Regensburg (DE)

( * ) Notice: Subject to any disclaimer, the term of this patent is extended or adjusted under 35 U.S.C. 154(b) by 133 days.

(21) Appl. No.: 12/472,578

(22) Filed: May 27, 2009

(65) Prior Publication Data

US 2010/0304369 A1    Dec. 2, 2010

(51) Int. Cl.
 *C12Q 1/68*  (2006.01)
 *C12P 19/34* (2006.01)
 *C07H 21/04* (2006.01)

(52) U.S. Cl. .................. 435/6.12; 435/91.2; 435/287.2; 536/24.3

(58) Field of Classification Search .............. 435/6.12, 435/91.2, 287.2; 536/24.3
See application file for complete search history.

(56) References Cited

U.S. PATENT DOCUMENTS

2006/0281120 A1\* 12/2006 Gorin et al. ........................ 435/6

FOREIGN PATENT DOCUMENTS

CN    101550451    \* 10/2009

OTHER PUBLICATIONS

Nucleic acid sequence search reports, accesion No. AXQ89843, EU427539.\*
Lowe et al., Nucleic Acid Research, vol. 18(7), 1990.\*
Fritsche, L.G. et al., Nature Genetics, 40(7):892-896 (2008). "Age-related macular degeneration is associated with an unstable ARMS2 (LOC387715) mRNA."
ABI Prism Genetic Analyser User Reference Guide, Applied Biosystems, 2002.
Altschul et al., J Mol Biol, 215:403-410 (1990). "Basic local alignment search tool."
Genbank Accession: NT_030059.12, Int. Human Genome Seq. Con., Mar. 2006.
Gu et al., Molecular & Cellular Proteomics, 8:1338-1349 (2009). "Assessing susceptibility to age-related macular degeneration with proteomic and genomic biomarkers."

\* cited by examiner

*Primary Examiner* — Kenneth R. Horlick
*Assistant Examiner* — Joyce Tung
(74) *Attorney, Agent, or Firm* — Nixon Peabody LLP

(57) ABSTRACT

Disclosed is a method for identifying an individual who has an altered risk for developing age-related macular degeneration comprising detecting an insertion/deletion polymorphism in the ARMS2 gene.

3 Claims, 5 Drawing Sheets

METHOD AND APPARATUS FOR DIAGNOSING AGE-RELATED MACULAR DEGENERATION

FIELD OF THE INVENTION

The present invention generally relates to a method and apparatus for diagnosing age-related macular degeneration in a human subject. In particular, the present invention relates to a method and apparatus for detecting an insertion/deletion polymorphism in the Age-Related Maculopathy Susceptibility 2 (ARMS2) gene for diagnosing a subject with age-related macular degeneration (AMD).

BACKGROUND OF THE INVENTION

Age-related macular degeneration (AMD) causes progressive impairment of central vision and is the leading cause of irreversible vision loss in older Americans (Swaroop A et al., 2007, Hum Mol Genet 16 Spec 2:R174-82). The most severe form of AMD involves neovascular/exudative (wet) and/or atrophic (dry) changes to the macula. Although the etiology of AMD remains largely unknown, implicated risk factors include age, ethnicity, smoking, hypertension, obesity and diet (Ambati J et al., 2003, Surv Opthalmol 48(3):257-93). Familial aggregation (Klaver C C et al., 1998, Arch Opthalmol 116(5):653-8), twin studies (Hammond C J et al., 2002, Opthalmology 109(4):730-6), and segregation analysis (Heiba I M et al., 1994, 11(1):51-67) suggest that there is also a significant genetic contribution to the disease. The candidate gene approach and genome-wide association studies have consistently implicated the complement factor H (CFH), third component of complement (C3) and second component of complement/factor B (C2/BF) genes, all members of the complement-mediated inflammatory cascade, as well as Age-Related Maculopathy Susceptibility 2 (ARMS2), a gene likely involved in mitochondria-associated pathways.

Much progress has been made in identifying and characterizing the genetic basis of AMD. In a remarkable example of the convergence of methods for disease gene discovery, multiple independent research efforts identified the Y402H variant in the complement factor H (CFH [(MIM 134370]) gene on chromosome 1q32 as the first major AMD susceptibility allele (Haines J L et al., 2005, Science 308(5720):419-21; Hageman G S et al., 2005, Proc Natl Acad Sci USA 102(20): 7227-32; Klein R J et al., 2005, Science 308(5720):385-9; Edwards A O et al., 2005, Science 308(5720):421-4; Zareparsi S et al., 2005, Am J Hum Genet 77(1):149-53; Jakobsdottir J et al., 2005, Am J Hum Genet 77(3):389-407). While one of the studies was able to pinpoint CFH on the basis of a whole-genome association study (Klein R J et al., supra), most studies focused on the 1q32 region because it had consistently been implicated by several whole-genome linkage scans. More recently, disease associated haplotypes within the CFH gene have also been shown to be associated with AMD (Li M et al., 2006, Nat Genet 38(9):1049-54). A second genomic region with similarly consistent linkage evidence is chromosome 10q26, which was identified as the single most promising region by a recent meta-analysis of published linkage screens (Fisher S A et al., 2005, Hum Mol Genet 14(15):2257-64).

Two other studies have suggested specific AMD susceptibility genes located on chromosome 10q26. One used a combination of family-based and case-control analyses to implicate the PLEKHA1 gene (pleckstrin homology domain containing, family A (phosphoinositide binding specific) member 1 [MIM 607772]) and the predicted ARMS2 gene (Jakobsdottir J et al., supra). ARMS2 appears to be a mitochondrial membrane protein with unknown function (Kanda A et al., 2007, Proc Natl Acad Sci USA 104(41):16227-32). A second study using two independent case-control datasets concluded that the T allele of SNP rs10490924 in ARMS2, a coding change (Ala69Ser) in exon 1 of this gene, was associated with AMD (Rivera A et al., 2005, Human Mol Genet 14(210:3227-36). Both studies reported that the chromosome 10q26 variant confers an AMD risk similar in magnitude to that of the Y402H variant in CFH. A locus with less strong association, but reproducible association is the complement component 2 (C2) and Factor B (C2/BF) locus within the major histocompatability complex III locus found on chromosome 6. The L9H variant of BF and the E318D variant of C2, as well as a variant in intron 10 of C2 and the R32Q variant of BF, confer a significantly reduced risk of AMD (Gold B et al., 2006, Nat Genet 38(4):458-62). Similarly, a highly significant association with AMD and SNPs within the C3 gene on chromosome 19p13.3-p13.2, specifically rs2230199 (Arg80Gly), was established recently (Yates et al., 2007, N Engl J Med 357(6):553-61).

There is a continuing need in the art to identify individual genes that are involved in the pathogenesis of AMD and/or to identify particular functional alleles that are directly involved in the pathogenesis of AMD, as well as to identify the interaction of the genes with modifiable behaviors.

SUMMARY OF THE INVENTION

According to an aspect of the present invention, there is provided a method for diagnosing a susceptibility to age-related macular degeneration in a human subject. The method comprising the steps of: amplifying a nucleic acid sequence containing position 3143 of SEQ ID NO. 1 using a first primer that binds upstream of said position and a second primer that binds downstream of said position; detecting an insertion/deletion polymorphism starting at position 3143 of SEQ ID NO. 1; and determining the genotype of the subject at position 3143 of SEQ ID NO. 1, wherein a homozygote for the insertion/deletion polymorphism is predictive of susceptibility to age-related macular degeneration and a heterozygote for the insertion/deletion polymorphism is predictive of a carrier for susceptibility to age-related macular degeneration.

In an embodiment, the insertion/deletion polymorphism comprises deletion of a nucleic acid sequence from position 3143 of SEQ ID NO. 1 to position 3585 of SEQ ID NO. 1 and insertion of a sequence from position 104 of SEQ ID NO. 2 to position 157 of SEQ ID NO. 2 in place of the deleted sequence.

In another embodiment, the insertion/deletion polymorphism is *372_815delins54.

In a further embodiment, the insertion/deletion polymorphism is detected by hybridization, chemical cleavage, direct DNA sequencing, use of restriction enzymes or Southern blotting.

In yet a further embodiment, the method comprises the step of obtaining a biological sample containing nucleic acid from the human subject prior to detecting the insertion/deletion polymorphism.

According to another aspect of the present invention, there is provided a method for diagnosing a susceptibility to age-related macular degeneration in a human subject. The method comprising the steps of: detecting the presence of mRNA corresponding to the age-related maculopathy susceptibility 2 (ARMS2) gene in a sample obtained from the human subject, wherein the absence of mRNA corresponding to the ARMS2 gene is predictive of susceptibility to age-related macular degeneration.

In an embodiment, the mRNA is detected by Northern blot analysis, nuclease protection assays, in situ hybridization or reverse-transcriptase polymerase chain reaction.

According to further aspect of the present invention, there is provided an apparatus for detecting a nucleotide in a nucleic acid sequence, the apparatus comprising: a substrate; and a first oligonucleotide bound to the substrate, the first oligonucleotide comprising a contiguous nucleic acid sequence complementary to SEQ ID NO. 1 containing position 3143 of the sequence.

In an embodiment, the apparatus further comprising a second oligonucleotide bound to the substrate, the second oligonucleotide comprising a contiguous nucleic acid sequence complementary to SEQ ID NO. 2 containing position 104 of the sequence.

In another embodiment, the first and second oligonucleotides comprises 25-mer contiguous nucleic acid sequences.

In a further embodiment, the first and second oligonucleotide comprises 60-mer contiguous nucleic acid sequences.

According to another aspect of the present invention, there is provided a nucleic acid comprising a sequence selected from the group consisting of: a) a nucleic acid sequence comprising SEQ ID NO. 3 or 4; b) a complement of a nucleic acid sequence comprising SEQ ID NO. 3 or 4; c) a fragment of either a) or b); d) a nucleic acid sequence capable of hybridizing to any one of a), b) or c); and e) a nucleic acid sequence that exhibits greater than about 70% sequence identity with the nucleic acids defined in a), b) or c).

According to an aspect of the present invention, there is provided a method of predicting susceptibility to age-related macular degeneration in a human subject, comprising the steps of: obtaining a biological sample from the human subject; exposing the biological sample to an antibody that recognizes a polypeptide corresponding to the age-related macular degeneration susceptibility 2 (ARMS2) gene; and detecting the presence of the antibody/polypeptide complex, wherein the absence of binding between the antibody and the polypeptide is predictive of susceptibility to age-related macular degeneration.

In one embodiment, the polypeptide is VLDPGVG (SEQ ID NO. 5).

In another embodiment, the presence of the antibody/polypeptide complex is detected by immunoblotting, immunoprecipitation, enzyme-linked immunosorbent assay (ELISA) or NMR spectrometry.

According to another aspect of the present invention, there is provided an antibody or fragment thereof that specifically binds the polypeptide VLDPGVG (SEQ ID NO. 5).

According to a further aspect of the present invention, there is provided a system for analyzing a biological sample comprising: a) a determination module configured to receive a biological sample and to determine sequence information, wherein the sequence information comprises: expression of age-related maculopathy susceptibility 2 (ARMS2) gene or an insertion/deletion polymorphism starting at position 3143 of SEQ ID NO. 1; c) a storage device configured to store sequence information from the determination module; d) a comparison module adapted to compare the sequence information stored on the storage device with reference data, and to provide a comparison result, wherein the comparison result is a level of ARMS2 gene expression compared to the reference data or is the presence or absence of the insertion/deletion polymorphism starting at position 3143 of SEQ ID NO.1; and e) a display module for displaying a content based in part on the comparison result for the user, wherein the content is a signal indicative of age-related macular degeneration.

According to an aspect of the present invention, there is provided a computer readable medium having computer readable instructions recorded thereon to define software modules including a comparison module and a display module for implementing a method on a computer, said method comprising: a) comparing with the comparison module the data stored on a storage device with reference data to provide a comparison result, wherein the comparison result is a level of ARMS2 gene expression compared to the reference data or is the presence or absence of the insertion/deletion polymorphism starting at position 3143 of SEQ ID NO.1; and b) displaying a content based in part on the comparison result for the user, wherein the content is a signal indicative of age-related macular degeneration.

BRIEF DESCRIPTION OF THE DRAWINGS

These and other features, aspects and advantages of the present invention will become better understood with regard to the following description and accompanying drawings wherein.

DETAILED DESCRIPTION OF THE INVENTION

The following description is of a preferred embodiment by way of example only and without limitation to the combination of feature necessary for carrying the invention into effect.

Figure 1:
FIG. 1 shows schematics of the wild-type ARMS2 gene (top) and the mutant ARMS2 gene (bottom)
Figure 1:
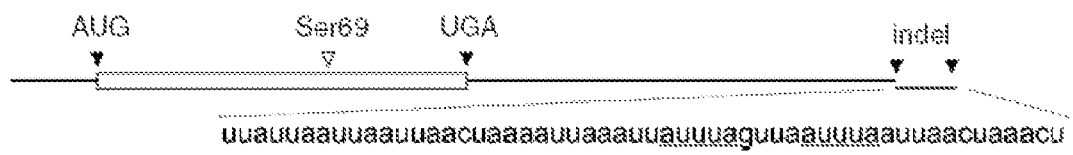

As shown in the following examples, an deletion-insertion (indel) polymorphism in the ARMS2 gene (NM-001099667.1:c.*372_815del443ins54) was shown to strongly associate with AMD. The indel polymorphism resides in the 3'-UTR of the ARMS2 gene and represents a combination of a deletion and insertion (*372_815delins54). The deletion removes the polyadenylation signal sequence at position *395_400 used for the addition of a poly(A) tract 19 by downstream (top panel of FIG. 1). The insertion introduces a 54-bp AU-rich element (bottom panel of FIG. 1), known for its properties to control mRNA decay in many transcripts that encode a wide variety of proteins involved in transient biological processes.

The present invention thus provides an indel variant associated with AMD, nucleic acid molecules containing the indel, as well as methods and reagents for the detection of the indel polymorphism. The age-related macular degeneration-associated indel disclosed herein is useful for diagnosing, screening for, and evaluating predisposition to age-related macular degeneration and related pathologies in humans.

The nucleic acid sequence of the human ARMS2 gene (SEQ ID NO. 1) contains a nucleic acid sequence from position 3143 to 3585, corresponding to the sequence shown in SEQ ID NO. 3, which is deleted or removed from the gene in those individuals susceptible to or having AMD. In place of this deleted sequence, a sequence of 54 nucleotides, shown in SEQ ID NO. 4, is inserted into the ARMS2 gene to produce the nucleic acid sequence shown in SEQ ID NO. 2.

As shown in Table 1, the indel polymorphism showed highly significant association with AMD compared to controls (42.2% vs 19.3%; P=4.1×10$^{-29}$). The odds ratio for the indel polymorphism showed a 2.9-fold increased risk of developing AMD in individuals carrying a single copy of the risk allele compared with an 8.1 fold increased risk in individuals carrying two copies of the risk allele. For the purposes of this invention, individuals carrying a single copy of the risk allele are considered heterozygotes, whereas individuals carrying two copies of the risk allele are considered homozygotes for the insertion/deletion polymorphism.

TABLE 1

| Marker | Gene | Role | Risk allele | Minor allele frequency | | Association results | |
| --- | --- | --- | --- | --- | --- | --- | --- |
| | | | | AMD (N = 760) | Control (N = 549) | Odds ratio (95% CI) | P value |
| del443ins54 | ARMS2 | 3' UTR | del443ins54 | 0.424 | 0.193 | 2.85 (2.37-3.43) | 4.1 × 10$^{-29}$ |

Association analyses were done using logistic regression assuming an additive model. Odds ratios are derived from logistic regression parameter estimates for a single copy of the risk allele.

Methods for identifying a risk of age-related macular degeneration in a subject include detecting the presence or absence of one or more of the polymorphisms described herein in a human nucleic acid sample.

Numerous methods exist for the measurement of specific polymorphism. Individuals carrying indel polymorphism may be detected at the DNA level by a variety of techniques. Nucleic acids for diagnosis may be obtained from a patient's cells, such as from blood, urine, saliva, tissue biopsy and autopsy material. The nucleic acid sample can be isolated from a biological sample using standard techniques. The nucleic acid sample may be isolated from the subject and then directly utilized in a method for determining the presence of a polymorphic variant, or alternatively, the sample may be isolated and then stored (e.g., frozen) for a period of time before being subjected to analysis.

Genomic DNA may be used directly for detection or may be amplified enzymatically by using PCR prior to analysis (Saiki RK et al., 1986, Nature 324(6093):163-6). As an example, PCR primers complementary to the nucleic acid of one or more polymorphic variants of the present invention can be used to identify and analyze the presence or absence of the polymorphic variant. For example, deletions and insertions can be detected by a change in size of the amplified product in comparison to the normal genotype. Polymorphic forms of the ARMS2 gene, specifically c.*372_815del443ins54 can be identified by hybridizing amplified DNA to radiolabeled RNA of the present invention or alternatively, radiolabeled antisense DNA sequences of the present invention. Perfectly matched sequences can be distinguished from mismatched duplexes by RNase A digestion or by differences in melting temperatures.

Sequence differences between a reference gene and genes having the indel polymorphism also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with a double-stranded PCR product or a single-stranded template molecule generated by a modified PCR technique. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (Myers R M et al., 1985, Science 230(4731): 1242-6).

Sequence changes at specific locations also may be revealed by nuclease protection assays, such as RNase and S1 protection or the chemical cleavage method (Cotton R G et al., 1988, Proc Natl Acad Sci USA 85(12):4397-401).

Thus, the detection of a specific DNA sequence may be achieved by methods which include, but are not limited to, hybridization, chemical cleavage, direct DNA sequencing or the use of restriction enzymes, (e.g., restriction fragment length polymorphisms ("RFLP")) and Southern blotting of genomic DNA. In addition, RNA or mRNA expression levels may be specifically determined by a number of different methods, including, but not limited to nuclease protection methods, Northern blot analysis, in situ hybridization or reverse-transcriptase polymerase chain reaction.

In addition to more conventional gel-electrophoresis and DNA sequencing, mutations also can be detected by in situ analysis.

In addition, the presence or absence of the indel polymorphism can be determined using one or both chromosomal complements represented in the nucleic acid sample. Determining the presence or absence of a polymorphic variant in both chromosomal complements represented in a nucleic acid sample is useful for determining the zygosity of an individual for the polymorphic variant (i.e., whether the individual is homozygous or heterozygous for the polymorphic variant). Any oligonucleotide-based diagnostic may be utilized to determine whether a sample includes the presence or absence of a polymorphic variant in a sample. For example, primer extension methods, ligase sequence determination methods (e.g., U.S. Pat. Nos. 5,679,524 and 5,952,174, and WO 01/27326), mismatch sequence determination methods (e.g., U.S. Pat. Nos. 5,851,770; 5,958,692; 6,110,684; and 6,183, 958), microarray sequence determination methods, restriction fragment length polymorphism (RFLP), single strand conformation polymorphism detection (SSCP) (e.g., U.S. Pat. Nos. 5,891,625 and 6,013,499), PCR-based assays (e.g., TAQMAN™ PCR System (Applied Biosystems)), and nucleotide sequencing methods may be used.

Oligonucleotide extension methods typically involve providing a pair of oligonucleotide primers in a polymerase chain reaction (PCR) or in other nucleic acid amplification methods for the purpose of amplifying a region from the nucleic acid sample that comprises the polymorphic variation. One oligonucleotide primer is complementary to a region 3' or downstream of the polymorphism and the other is complementary to a region 5' or upstream of the polymorphism. A PCR primer pair may be used in methods disclosed in U.S. Pat. Nos. 4,683,195; 4,683,202; 4,965,188; 5,656,493; 5,998,143; 6,140,054; WO 01/27327; and WO 01/27329 for example. PCR primer pairs may also be used in any commercially available machines that perform PCR, such as any of the GENEAMP™, systems available from Applied Biosystems. Also, those of ordinary skill in the art will be able to design oligonucleotide primers based upon the nucleotide sequences set forth in SEQ ID NOs:1 and 2.

Also provided is an extension oligonucleotide that hybridizes to the amplified fragment adjacent to the polymorphic variation. An adjacent fragment refers to the 3' end of the extension oligonucleotide being often 1 nucleotide from the 5' end of the polymorphic site, and sometimes 2, 3, 4, 5, 6, 7, 8, 9, or 10 nucleotides from the 5' end of the polymorphic site, in the nucleic acid when the extension oligonucleotide is hybridized to the nucleic acid. The extension oligonucleotide then is extended by one or more nucleotides, and the number and/or type of nucleotides that are added to the extension oligonucleotide determine whether the polymorphic variant is present. Oligonucleotide extension methods are disclosed, for example, in U.S. Pat. Nos. 4,656,127; 4,851,331; 5,679,524; 5,834,189; 5,876,934; 5,908,755; 5,912,118; 5,976,802; 5,981,186; 6,004,744; 6,013,431; 6,017,702; 6,046,005; 6,087,095; 6,210,891; and WO 01/20039. Oligonucleotide extension methods using mass spectrometry are described, for example, in U.S. Pat. Nos. 5,547,835; 5,605,798; 5,691,141; 5,849,542; 5,869,242; 5,928,906; 6,043,031; and 6,194,144. Multiple extension oligonucleotides may be utilized in one reaction, which is referred to as multiplexing.

Genetic mutations can be identified by hybridizing a sample and control nucleic acids, e.g., DNA or RNA, to high density arrays containing hundreds or thousands of oligonucleotides probes (Cronin M T et al., Hum Mutat 7(3):244-55; Kozal M J et al., 1996, Nat Med 2(7):753-9). For example, genetic mutations can be identified in two-dimensional arrays containing light-generated DNA probes as described in Cronin et al., (supra). Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene. Specific mutations can also be determined through direct sequencing of one or both strands of DNA using dideoxy nucleotide chain termination chemistry, electrophoresis through a semi-solid matrix and fluorescent or radioactive chain length detection techniques. Further mutation detection techniques may involve differential susceptibility of the polymorphic double strand to restriction endonuclease digestion, or altered electrophoretic gel mobility of single or double stranded gene fragments containing one polymorphic form. Other techniques to detect specific DNA polymorphisms or mutation may involve evaluation of the structural characteristics at the site of polymorphism using nuclear magnetic resonance or x-ray diffraction techniques.

An apparatus for detecting a nucleotide in a nucleic acid sequence is provided. The apparatus comprises a substrate, such as a glass slide, and at least one oligonucleotide bound to the substrate. The oligonucleotide comprising a contiguous nucleic acid sequence complementary to SEQ ID NO. 1 and containing position 3143 of the sequence or complementary to SEQ ID NO. 2 and containing position 104 of the sequence. In most cases, a second oligonucleotide will be bound to the substrate which corresponds to the oligonucleotide not already bound to the substrate. Preferably, the substrate will contain at least an oligonucleotide comprising a contiguous nucleic acid sequence complementary to SEQ ID NO. 1 and containing position 3143 of the sequence and an oligonucleotide comprising a contiguous nucleic acid sequence complementary to SEQ ID NO. 2 and containing position 104 of the sequence.

Although the length of the oligonucleotides for use with the apparatus can be chosen in part based on the overall characteristics of the oligonucleotides on the substrate, a preferred range of lengths are between 25-mer and 60-mer.

A microarray can be utilized for determining whether the indel polymorphism is present or absent in a nucleic acid sample. A microarray may include any oligonucleotides described hereinabove, and methods for making and using oligonucleotide microarrays suitable for diagnostic use are disclosed in U.S. Pat. Nos. 5,492,806; 5,525,464; 5,589,330; 5,695,940; 5,849,483; 6,018,041; 6,045,996; 6,136,541; 6,142,681; 6,156,501; 6,197,506; 6,223,127; 6,225,625; 6,229,911; 6,239,273; WO 00/52625; WO 01/25485; and WO 01/29259. The microarray typically comprises a solid support and the oligonucleotides may be linked to this solid support by covalent bonds or by non-covalent interactions. The oligonucleotides may also be linked to the solid support directly or by a spacer molecule. A microarray may comprise one or more oligonucleotides complementary to a indel polymorphism.

These genetic tests are useful for prognosing and/or diagnosing AMD and often are useful for determining whether an individual is at an increased or decreased risk of developing or having AMD.

Results from prognostic tests may be combined with other test results to diagnose AMD. For example, prognostic results may be gathered, a patient sample may be ordered based on a determined predisposition to AMD, the patient sample analyzed, and the results of the analysis may be utilized to diagnose AMD. Also AMD diagnostic methods can be developed from studies used to generate prognostic/diagnostic methods in which populations are stratified into subpopulations having different progressions of AMD. In another embodiment, prognostic results may be gathered; a patient's risk factors for developing AMD analyzed (e.g., age, family history, smoking); and a patient sample may be ordered based on a determined predisposition to AMD. In an alternative embodiment, the results from predisposition analyses may be combined with other test results, epidemiologic or genetic in nature, indicative of AMD, which were previously, concurrently, or subsequently gathered with respect to the predisposition testing. In these embodiments, the combination of the prognostic test results with other test results can be probative of AMD, and the combination can be utilized as an AMD diagnostic.

A kit also may be utilized for determining whether the indel polymorphism is present or absent in a nucleic acid sample. A kit can include one or more pairs of oligonucleotide primers useful for amplifying a fragment of a nucleotide sequence of interest, where the fragment includes a polymorphic site. The kit sometimes comprises a polymerizing agent, for example, a thermostable nucleic acid polymerase such as one disclosed in U.S. Pat. No. 4,889,818 or 6,077,664. Also, the kit often comprises an elongation oligonucleotide that hybridizes to the nucleotide sequence in a nucleic acid sample adjacent to the polymorphic site. Where the kit includes an elongation oligonucleotide, it can also include chain elongating nucleotides, such as dATP, dTTP, dGTP, dCTP, and dITP, including analogs of dATP, dTTP, dGTP, dCTP and dITP, provided that such analogs are substrates for a thermostable nucleic acid polymerase and can be incorporated into a nucleic acid chain elongated from the extension oligonucleotide. Along with chain elongating nucleotides would be one or more chain terminating nucleotides such as ddATP, ddTTP, ddGTP, ddCTP. The kit can include one or more oligonucleotide primer pairs, a polymerizing agent, chain elongating nucleotides, at least one elongation oligonucleotide, and one or more chain terminating nucleotides. Kits optionally include buffers, vials, microtiter plates, and instructions for use.

Individuals carrying indel polymorphism of the present invention may be detected at the protein level by a variety of techniques, including, but not limited to, immunoblotting, immunoprecipitation, and enzyme-linked immunosorbent assay (ELISA). As shown below in the examples, individuals having two copies of the indel polymorphism, or are homozygous for the indel polymorphism, have limited to no detectable levels of ARMS2 protein. Accordingly, contacting a polypeptide or protein encoded by a nucleotide sequence from a subject with an antibody that specifically binds to an epitope associated with an altered, usually increased risk of AMD in the polypeptide can be used to determine whether an individual has or is susceptible to developing AMD. Cells suitable for diagnosis may be obtained from a patient's blood, urine, saliva, tissue biopsy and autopsy material.

An immunogen typically is used to prepare antibodies by immunizing a suitable subject (e.g., rabbit, goat, mouse or other mammal). An appropriate immunogenic preparation can contain, for example, recombinantly expressed chemically synthesized polypeptide. The preparation can further include an adjuvant, such as Freund's complete or incomplete adjuvant, or a similar immunostimulatory agent. Amino acid polymorphisms can be detected using antibodies specific for the altered epitope by western analysis after the electrophoresis of denatured proteins. Protein polymorphism can also be detected using fluorescently identified antibodies which bind to specific polymorphic epitopes and detected in whole cells using fluorescence activated cell sorting techniques (FACS). Polymorphic protein sequence may also be determined by NMR spectroscopy or by x-ray diffraction studies. Further, determination of polymorphic sites in proteins may be accomplished by observing differential cleavage by specific or non specific proteases.

An antibody is an immunoglobulin molecule or immunologically active portion thereof, i.e., an antigen-binding portion. Examples of immunologically active portions of immunoglobulin molecules include F(ab) and F(ab')$_2$ fragments which can be generated by treating the antibody with an enzyme such as pepsin. An antibody can be polyclonal, monoclonal, or recombinant (e.g., a chimeric or humanized), fully human, non-human (e.g., murine), or a single chain antibody. An antibody may have effector function and can fix complement, and is sometimes coupled to a toxin or imaging agent.

A full-length polypeptide or antigenic peptide fragment encoded by a target nucleotide sequence can be used as an immunogen or can be used to identify antibodies made with other immunogens, e.g., cells, membrane preparations, and the like. An antigenic peptide often includes at least 8 amino acid residues of the amino acid sequences encoded by a nucleotide sequence of one of SEQ ID NOs:1 and 3, and encompasses an epitope. Antigenic peptides sometimes include 10 or more amino acids, 15 or more amino acids, 20 or more amino acids, or 30 or more amino acids. Hydrophilic and hydrophobic fragments of polypeptides sometimes are used as immunogens.

Epitopes encompassed by the antigenic peptide are regions located on the surface of the polypeptide (e.g., hydrophilic regions) as well as regions with high antigenicity. For example, an Emini surface probability analysis of the human polypeptide sequence can be used to indicate the regions that have a particularly high probability of being localized to the surface of the polypeptide and are thus likely to constitute surface residues useful for targeting antibody production. The antibody may bind an epitope on any domain or region on polypeptides for use in the invention.

Also, chimeric, humanized, and completely human antibodies are useful for applications which include repeated administration to subjects. Chimeric and humanized monoclonal antibodies, comprising both human and non-human portions, can be made using standard recombinant DNA techniques. Such chimeric and humanized monoclonal antibodies can be produced by recombinant DNA techniques, for example using methods described in WO87/002671; Akira, et al., European Patent Application 184,187; Taniguchi, M., European Patent Application 171,496; Morrison et al., European Patent Application 173,494; Neuberger et al., PCT International Publication No. WO 86/01533; Cabilly et al., U.S. Pat. No. 4,816,567; Cabilly et al., European Patent Application 125,023; Better M et al., 1988, Science 240(4855):1041-3; Liu et al., 1987 Proc Natl Acad Sci USA 84(10):3439-43; Liu et al., 1987, J Immunol 139(10):3521-6; Sun LK et al., 1987, Proc Natl Acad Sci USA 84(1):214-8; Nishimura Y et al., Cancer Res 47(4):999-1005; Wood Cr et al., 1985, Nature 314(6010):446-9; Shaw D R et al., 1988, J Natl Cancer Inst 80(19):1553-9; Morrison S L, 1985, Science 229(4719):1202-7; Winter U.S. Pat. No. 5,225,539; Verhoeyen M et al., 1988, Science 239(4847):1534-6; and Beidler C B et al., 1988, J Immunol 141(11):4053-60.

An antibody can be a single chain antibody. A single chain antibody (scFV) can be engineered (see, e.g., Colcher et al. 1999, Ann NY Acad Sci 880:263-80 and Reiter et al., 1996, Clin Cancer Res 2(2):245-52). Single chain antibodies can be dimerized or multimerized to generate multivalent antibodies having specificities for different epitopes of the same target polypeptide.

Antibodies also may be selected or modified so that they exhibit reduced or no ability to bind an Fc receptor. For example, an antibody may be an isotype or subtype, fragment or other mutant, which does not support binding to an Fc receptor (e.g., it has a mutagenized or deleted Fc receptor binding region).

An antibody (e.g., monoclonal antibody) can be used to isolate target polypeptides by standard techniques, such as affinity chromatography or immunoprecipitation. Moreover, an antibody can be used to detect a target polypeptide (e.g., in a cellular lysate or cell supernatant) in order to evaluate the abundance and pattern of expression of the polypeptide. Antibodies can be used diagnostically to monitor polypeptide levels in tissue as part of a clinical testing procedure, e.g., to determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H. Also, an antibody can be utilized as a test molecule for determining whether it can treat age-related macular degeneration, and as a therapeutic for administration to a subject for treating age-related macular degeneration.

An antibody can be made by immunizing with a purified antigen, or a fragment thereof, a membrane associated antigen, tissues, e.g., crude tissue preparations, whole cells, preferably living cells, lysed cells, or cell fractions.

Included as part of this invention are antibodies which bind only a native polypeptide, only denatured or otherwise non-native polypeptide, or which bind both, as well as those having linear or conformational epitopes. Conformational epitopes sometimes can be identified by selecting antibodies that bind to native but not denatured polypeptide. Also featured are antibodies that specifically bind to a polypeptide variant associated with AMD.

A therapeutic formulation based on the findings of the present invention can be administered to a subject in need of a therapeutic for treating AMD. Therapeutic formulations can be administered by any of the paths described herein. With regard to prophylactic and therapeutic methods of treatment, such treatments may be specifically tailored or modified, based on the knowledge obtained from pharmacogenomic analyses described herein.

A treatment is the application or administration of a therapeutic formulation to a subject, or application or administration of a therapeutic agent to an isolated tissue or cell line from a subject with the purpose to cure, heal, alleviate, relieve, alter, remedy, ameliorate, improve or affect AMD, symptoms of AMD or a predisposition towards AMD. A therapeutic formulation of the present invention includes small molecules, peptides, antibodies, ribozymes and antisense oligonucleotides. Administration of a therapeutic formulation can occur prior to the manifestation of symptoms characteristic of AMD, such that the cancer is prevented or delayed in its progression. The appropriate therapeutic composition can be determined based on screening assays described herein.

As discussed, successful treatment of AMD can be brought about by techniques that serve to agonize ARMS2 expression or function. These techniques include administration of modulators that include, but are not limited to, small organic or inorganic molecules; antibodies (including, for example, polyclonal, monoclonal, humanized, anti-idiotypic, chimeric or single chain antibodies, and FAb, F(ab')2 and FAb expression library fragments, scFV molecules, and epitope-binding fragments thereof); and peptides, phosphopeptides or polypeptides.

Embodiments of the invention also provide for systems 10 (and computer readable media 151 for causing computer systems) to perform a method for determining whether an individual has AMD or a pre-disposition for AMD based on expression profiles or sequence information.

Embodiments of the invention have been described through functional modules, which are defined by computer executable instructions recorded on computer readable media and which cause a computer to perform method steps when executed. The modules have been segregated by function for the sake of clarity. However, it should be understood that the modules need not correspond to discreet blocks of code and the described functions can be carried out by the execution of various code portions stored on various media and executed at various times. Furthermore, it should be appreciated that the modules may perform other functions, thus the modules are not limited to having any particular functions or set of functions.

The computer readable media 151 can be any available tangible media that can be accessed by a computer 250. Computer readable media 151 includes volatile and nonvolatile, removable and non-removable tangible media implemented in any method or technology for storage of information such as computer readable instructions, data structures, program modules or other data. Computer readable media includes, but is not limited to, RAM (random access memory), ROM (read only memory) 230, EPROM (eraseable programmable read only memory), EEPROM (electrically eraseable programmable read only memory), flash memory or other memory technology 240, CD-ROM (compact disc read only memory), DVDs (digital versatile disks) or other optical storage media, magnetic cassettes, magnetic tape, magnetic disk storage or other magnetic storage media, other types of volatile and non-volatile memory, and any other tangible medium which can be used to store the desired information and which can accessed by a computer including and any suitable combination of the foregoing.

Computer-readable data embodied on one or more computer-readable media 151 may define instructions, for example, as part of one or more programs, that, as a result of being executed by a computer, instruct the computer to perform one or more of the functions described herein (e.g., in relation to system 10, or computer readable medium 151), and/or various embodiments, variations and combinations thereof. Such instructions may be written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable media 151 on which such instructions are embodied may reside on one or more of the components of either of system 10, or computer readable medium 151 described herein, may be distributed across one or more of such components, and may be in transition there between.

The computer-readable media 151 may be transportable such that the instructions stored thereon can be loaded onto any computer resource to implement the aspects of the present invention discussed herein. In addition, it should be appreciated that the instructions stored on the computer-readable medium 151, described above, are not limited to instructions embodied as part of an application program running on a host computer. Rather, the instructions may be embodied as any type of computer code (e.g., software or microcode) that can be employed to program a computer to implement aspects of the present invention. The computer executable instructions may be written in a suitable computer language or combination of several languages. Basic computational biology methods are known to those of ordinary skill in the art and are described in, for example, Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medi-* cine (CRC Press, London, 2000) and Ouelette and Bzevanis *Bioinformatics: A Practical Guide for Analysis of Gene and Proteins* (Wiley & Sons, Inc., 2$^{nd}$ ed., 2001).

The functional modules of certain embodiments of the invention include a determination module 40, a storage device 30, a comparison module 80 and a display module 110. The functional modules can be executed on one, or multiple, computers, or by using one, or multiple, computer networks. The determination module 40 has computer executable instructions to provide sequence information in computer readable form 50. As used herein, "sequence information" refers to any nucleotide and/or amino acid sequence, including but not limited to full-length nucleotide and/or amino acid sequences, partial nucleotide and/or amino acid sequences, or mutated sequences. Moreover, information "related to" the sequence information includes detection of the presence or absence of a sequence (e.g., detection of a mutation or deletion), determination of the concentration of a sequence in the sample (e.g., amino acid sequence expression levels, or nucleotide (RNA or DNA) expression levels), and the like. The term "sequence information" is intended to include the presence or absence of post-translational modifications (e.g. phosphorylation, glycosylation, summylation, farnesylation, and the like).

As an example, determination modules for determining sequence information may include known systems for automated sequence analysis including but not limited to Hitachi FMBIO® and Hitachi FMBIO® II Fluorescent Scanners (available from Hitachi Genetic Systems, Alameda, Calif.); Spectrumedix® SCE 9610 Fully Automated 96-Capillary Electrophoresis Genetic Analysis Systems (available from SpectruMedix LLC, State College, Pa.); ABI PRISM® 377 DNA Sequencer, ABI® 373 DNA Sequencer, ABI PRISM® 310 Genetic Analyzer, ABI PRISM® 3100 Genetic Analyzer, and ABI PRISM® 3700 DNA Analyzer (available from Applied Biosystems, Foster City, Calif.); Molecular Dynamics FluorImager™ 575, SI Fluorescent Scanners, and Molecular Dynamics FluorImager™ 595 Fluorescent Scanners (available from Amersham Biosciences UK Limited, Little Chalfont, Buckinghamshire, England); GenomyxSC™ DNA Sequencing System (available from Genomyx Corporation (Foster City, Calif.); and Pharmacia ALF™ DNA Sequencer and Pharmacia ALFexpress™ (available from Amersham Biosciences UK Limited, Little Chalfont, Buckinghamshire, England).

Alternative methods for determining sequence information include systems for protein analysis. For example, mass spectrometry systems including Matrix Assisted Laser Desorption Ionization—Time of Flight (MALDI-TOF) systems and SELDI-TOF-MS ProteinChip array profiling systems; systems for analyzing gene expression data (see, for example, published U.S. Patent Application, Pub. No. U.S. 2003/0194711); systems for array based expression analysis: e.g., HT array systems and cartridge array systems such as GeneChip® AutoLoader, Complete GeneChip® Instrument System, GeneChip® Fluidics Station 450, GeneChip® Hybridization Oven 645, GeneChip® QC Toolbox Software Kit, GeneChip® Scanner 3000 7G plus Targeted Genotyping System, GeneChip® Scanner 3000 7G Whole-Genome Association System, GeneTitan™ Instrument, and GeneChip® Array Station (each available from Affymetrix, Santa Clara, Calif.); automated ELISA systems (e.g., DSX® or DS2® (available from Dynax, Chantilly, Va.) or the Triturus® (available from Grifols USA, Los Angeles, Calif.), The Mago® Plus (available from Diamedix Corporation, Miami, Fla.); Densitometers (e.g. X-Rite-508-Spectro Densitometer® (available from RP Imaging™, Tucson, Ariz.), The HYRYS™ 2 HIT densitometer (available from Sebia Electrophoresis, Norcross, Ga.); automated Fluorescence insitu hybridization systems (see for example, U.S. Pat. No. 6,136,540); 2D gel imaging systems coupled with 2-D imaging software; microplate readers; Fluorescence activated cell sorters (FACS) (e.g. Flow Cytometer FACSVantage SE, (available from Becton Dickinson, Franklin Lakes, N.J.); and radio isotope analyzers (e.g. scintillation counters).

The sequence information 40 determined in the determination module 40 can be read by the storage device 30. As used herein the "storage device" is intended to include any suitable computing or processing apparatus or other device configured or adapted for storing data or information. Examples of electronic apparatus suitable for use with the present invention include stand-alone computing apparatus, data telecommunications networks, including local area networks (LAN), wide area networks (WAN), Internet, Intranet, and Extranet, and local and distributed computer processing systems. Storage devices also include, but are not limited to: magnetic storage media, such as floppy discs, hard disc storage media, magnetic tape, optical storage media such as CD-ROM, DVD, electronic storage media such as RAM, ROM, EPROM, EEPROM and the like, general hard disks and hybrids of these categories such as magnetic/optical storage media. The storage device is adapted or configured for having recorded thereon sequence information or expression level information. Such information may be provided in digital form 220 that can be transmitted and read electronically, e.g., via the Internet, on diskette, via USB (universal serial bus) or via any other suitable mode of communication.

As used herein, "expression level information" refers to any nucleotide and/or amino acid expression level information, including but not limited to full-length nucleotide and/or amino acid sequences, partial nucleotide and/or amino acid sequences, or mutated sequences. Moreover, information "related to" the expression level information includes detection of the presence or absence of a sequence (e.g., presence or absence of an amino acid sequence, nucleotide sequence, or post translational modification), determination of the concentration of a sequence in the sample (e.g., amino acid sequence levels, or nucleotide (RNA or DNA) expression levels, or level of post translational modification), and the like.

As used herein, "stored" refers to a process for encoding information on the storage device. Those skilled in the art can readily adopt any of the presently known methods for recording information on known media to generate manufactures comprising the sequence information or expression level information.

A variety of software programs and formats can be used to store the sequence information or expression level information on the storage device. Any number of data processor structuring formats (e.g., text file or database) can be employed to obtain or create a medium having recorded thereon the sequence information or expression level information.

By providing sequence information or expression level information in computer-readable form, one can use the sequence information or expression level information in readable form in the comparison module 80 to compare a specific sequence or expression profile with the reference data within the storage device 30. For example, search programs can be used to identify fragments or regions of the sequences that match a particular sequence (reference data, e.g., sequence information obtained from a control sample) or direct comparison of the determined expression level can be compared to the reference data expression level (e.g., sequence information obtained from a control sample). The comparison made in computer-readable form provides a computer readable comparison result which can be processed by a variety of means 90. Content 100 based on the comparison result can be retrieved from the comparison module to indicate a predisposition or diagnosis of AMD.

In one embodiment the reference data stored in the storage device 30 to be read by the comparison module 80 is sequence information data obtained from a control biological sample of the same type as the biological sample to be tested. Alternatively, the reference data are a database, e.g., a part of the entire genome sequence of an organism, or a protein family of sequences, or an expression level profile (RNA, protein or peptide). In one embodiment the reference data are sequence information or expression level profiles that are indicative of a predisposition or diagnosis of AMD.

In one embodiment, the reference data are one or more reference polynucleotide, or polypeptide sequences selected from the group consisting of SEQ ID NO: 1, SEQ ID NO: 2, SEQ ID NO: 3, and SEQ ID NO: 4.

In one embodiment, the reference data are electronically or digitally recorded and annotated from databases including, but not limited to GenBank (NCBI) protein and DNA databases such as genome, ESTs, SNPS, Traces, Celara, Ventor Reads, Watson reads, HGTS, and the like; Swiss Institute of Bioinformatics databases, such as ENZYME, PROSITE, SWISS-2DPAGE, Swiss-Prot and TrEMBL databases; the Melanie software package or the ExPASy WWW server, and the like; the SWISS-MODEL, Swiss-Shop and other network-based computational tools; the Comprehensive Microbial Resource database (available from The Institute of Genomic Research). The resulting information can be stored in a relational data base that may be employed to determine homologies between the reference data or genes or proteins within and among genomes.

The "comparison module" 80 can use a variety of available software programs and formats for the comparison operative to compare sequence information determined in the determination module to reference data. In one embodiment, the comparison module 80 is configured to use pattern recognition techniques to compare sequence information from one or more entries to one or more reference data patterns. The comparison module 80 may be configured using existing commercially-available or freely-available software for comparing patterns, and may be optimized for particular data comparisons that are conducted. The comparison module 80 provides computer readable information related to the sequence information that can include, for example, detection of the presence or absence of a sequence (e.g., detection of a mutation or deletion (protein or DNA), information regarding distinct alleles, detection of post-translational modification, or omission or repetition of sequences); determination of the concentration of a sequence in the sample (e.g., amino acid sequence/protein expression levels, or nucleotide (RNA or DNA) expression levels, or levels of post-translational modification), or determination of an expression profile.

In one embodiment, the comparison module 80 permits the prediction of protein sequences from polynucleotide sequences, permits prediction of open reading frames (ORF), or permits prediction of homologous sequence information in comparison to reference data, i.e., homologous protein domains, homologous DNA or RNA sequences, or homologous exons and/or introns.

In one embodiment, the comparison module 80 uses sequence information alignment programs such as BLAST (Basic Local Alignment Seartch Tool) or FAST (using the Smith-Waternan algorithm) may be employed individually or in combination. These algorithms determine the alignment between similar regions of sequences and a percent identity between sequences. For example, alignment may be calculated by matching, bases-by-base or amino acid-by amino-acid.

The comparison module 80, or any other module of the invention, may include an operating system (e.g., UNIX) on which runs a relational database management system, a World Wide Web application, and a World Wide Web server. World Wide Web application includes the executable code necessary for generation of database language statements (e.g., Structured Query Language (SQL) statements). Generally, the executables will include embedded SQL statements. In addition, the World Wide Web application may include a configuration file which contains pointers and addresses to the various software entities that comprise the server as well as the various external and internal databases which must be accessed to service user requests. The Configuration file also directs requests for server resources to the appropriate hardware—as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). Thus, in a particular preferred embodiment of the present invention, users can directly access data (via Hypertext links for example) residing on Internet databases using a HTML interface provided by Web browsers and Web servers.

In one embodiment, the comparison module 80 performs comparisons with mass-spectometry spectra, for example comparisons of peptide fragment sequence information can be carried out using spectra processed in MATLB with script called "Qcealign" (see for example WO2007/022248, herein incorporated by reference) and "Qpeaks" (Spectrum Square Associates, Ithaca, N.Y.), or Ciphergen Peaks 2.1™ software. The processed spectra can then be aligned using alignment algorithms that align sample data to the control data using minimum entropy algorithm by taking baseline corrected data (see for example WIPO Publication WO2007/022248, herein incorporated by reference). The comparison result can be further processed by calculating ratios. Protein expression profiles can be discerned.

In one embodiment, computational algorithms such as expectation-maximization (EM), subtraction and PHASE are used in methods for statistical estimation of haplotypes (see, e.g., Clark, A. G. *Mol Biol Evol* 7:111-22 (1990); Stephens, M., Smith, N. J. & Donnelly, P. *Am J Hum Genet* 68:978-89 (2001); Templeton, A. R., Sing, C. F., Kessling, A. & Humphries, *Genetics* 120:1145-54 (1988)).

Various algorithms are available which are useful for comparing data and identifying the predictive gene signatures. For example, algorithms such as those identified in Xu et al., *Physiol. Genomics* 11:11-20 (2002). There are numerous software available for detection of SNPs and polymorphisms that can be used in the comparison module 80, including, but not limited to: HaploSNPer, a web-based program for detecting SNPs and alleles in user-specified input sequences from both diploid and polyploid species (available on the world-wide web at bioinformatics.nl/tools/haplosnper/; see also Tang et al., *BMC Genetics* 9:23 (2008)); Polybayes, a tool for SNP discovery in redundant DNA sequences (Marth, G T., et al., *Nature Genetics* 23(4):452-6 (1999); SSAHA-SNP, a polymorphism detection tool that uses the SSAHA alignment algorithm (available from Wellcome Trust Sanger Institute, Cambridge, United Kingdom, see also Ning Z., et al.,

*Genome Research* 11(10):1725-9 (2001)); Polyphred, A SNP discovery package built on phred, phrap, and consed tools (available on the world-wide web, see Nickerson, D A et al., *Nucleic Acids Research* 25(14):2745-51 (1997)); NovoSNP, a graphical Java-based program (PC/Mac/Linux) to identify SNPs and indels (available on the world-wide web, see Weckx, S. et al., *Genome Research* 15(3):436-442 (2005)); SNPdetector™, for automated identification of SNPs and mutations in fluorescence-based resequencing reads (available from Affymetrix, Santa Clara, Calif.), see also Zhang et al. *PLoS Comput Biol* (5):e53 (2005). SNPdetector runs on Unix/Linux platform and is available publicly; Affymetrix (Santa Clara, Calif.) has multiple data analysis software that can be used, for example Genotyping Console™ Software, GeneChip® Sequence Analysis Software (GSEQ), GeneChip® Targeted Genotyping Analysis Software (GTGS) and Expression Console™ Software.

In one embodiment, the comparison module 80 compares gene expression profiles. For example, detection of gene expression profiles can be determined using Affymetrix Microarray Suite software version 5.0 (MAS 5.0) (available from Affymetrix, Santa Clara, Calif.) to analyze the relative abundance of a gene or genes on the basis of the intensity of the signal from probe sets, and the MAS 5.0 data files can be transferred into a database and analyzed with Microsoft Excel and GeneSpring 6.0 software (available from Agilent Technologies, Santa Clara, Calif.). The detection algorithm of MAS 5.0 software can be used to obtain a comprehensive overview of how many transcripts are detected in given samples and allows a comparative analysis of 2 or more microarray data sets.

In one embodiment, the comparison module 80 compares protein expression profiles. Any available comparison software can be used, including but not limited to, the Ciphergen Express (CE) and Biomarker Patterns Software (BPS) package (available from Ciphergen Biosystems, Inc., Freemont, Calif.). Comparative analysis can be done with protein chip system software (e.g., The Proteinchip Suite (available from Bio-Rad Laboratories, Hercules, Calif.). Algorithms for identifying expression profiles can include the use of optimization algorithms such as the mean variance algorithm (e.g. JMP Genomics algorithm available from JMP Software Cary, N.C.).

In one embodiment of the invention, pattern comparison software is used to determine whether patterns of expression or mutations are indicative of a disease.

The comparison module 80 provides computer readable comparison result that can be processed in computer readable form by predefined criteria, or criteria defined by a user, to provide a content based in part on the comparison result that may be stored and output as requested by a user using a display module.

The content 100 based on the comparison result may be an expression profile of one or more proteins, or an expression profile of one or more genes. In one embodiment, the content 100 is a sequence of a particular gene or protein and a determination of the presence of one or more mutations, or specific post-translational modification. In one embodiment, the content 100 based on the comparison result is a signal indicative of the presence or absence of AMD.

In one embodiment of the invention, the content 100 based on the comparison result is displayed a on a computer monitor 120. In one embodiment of the invention, the content 100 based on the comparison result is displayed through printable media 130, 140. The display module 110 can be any suitable device configured to receive from a computer and display computer readable information to a user. Non-limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices of Sunnyvale, Calif., or any other type of processor, visual display devices such as flat panel displays, cathode ray tubes and the like, as well as computer printers of various types.

In one embodiment, a World Wide Web browser is used for providing a user interface for display of the content based on the comparison result. It should be understood that other modules of the invention can be adapted to have a web browser interface. Through the Web browser, a user may construct requests for retrieving data from the comparison module. Thus, the user will typically point and click to user interface elements such as buttons, pull down menus, scroll bars and the like conventionally employed in graphical user interfaces. The requests so formulated with the user's Web browser are transmitted to a Web application which formats them to produce a query that can be employed to extract the pertinent information related to the sequence information, e.g., display of an indication of the presence or absence of mutation or deletion (DNA or protein); display of expression levels of an amino acid sequence (protein); display of nucleotide (RNA or DNA) expression levels; display of expression, SNP, or mutation profiles, or haplotypes, or display of information based thereon. In one embodiment, the sequence information of the reference sample data is also displayed.

In one embodiment, the display module 110 displays the comparison result and whether the comparison result is indicative of a disease, e.g., whether the expression profile of ARMS2 mRNA or protein, or sequence having the indel polymorphism is indicative of AMD.

In one embodiment, the content 100 based on the comparison result that is displayed is a signal (e.g. positive or negative signal) indicative of the presence or absence of AMD, thus only a positive or negative indication may be displayed.

The present invention therefore provides for systems (and computer readable media for causing computer systems) to perform methods for determining whether an individual has AMD or a pre-disposition, for AMD based on expression profiles or sequence information.

System 10, and computer readable medium 151, are merely an illustrative embodiments of the invention for performing methods of determining whether an individual has a specific disease or disorder or a pre-disposition, for a specific disease or disorder based on expression profiles or sequence information, and is not intended to limit the scope of the invention. Variations of system 10, and computer readable medium 151, are possible and are intended to fall within the scope of the invention.

The modules of the machine, or used in the computer readable medium, may assume numerous configurations. For example, function may be provided on a single machine or distributed over multiple machines.

EXAMPLES

The case-control sample used in the study considered of 794 individuals with nonfamilial AMD (64.4% females; mean age 76.8±6.6) and 612 unrelated control individuals (62.1% females; mean age 76.2±5.3). All individuals originated from the Lower Franconian area in Bavaria, Southern Germany, and were exclusively recruited at the University Eye Clinic Würzburg. Criteria for inclusion and exclusion of cases and controls have been described elsewhere (Rivera A et al., 2005, Hum. Mol. Genet. 14:3227-3236).

Example 1

Genotyping of Samples

Genomic DNA was extracted from peripheral blood according to established protocols. 794 individuals with non-familial AMD and 612 unrelated controls were genotyped for the indel polymorphism *372_815delins54. All control genotypes were in Hardy-Weinberg equilibrium (P<0.1). Hardy-Weinberg equilibrium was assessed for cases and controls by simulation methods implemented in the Genetics package of R. Single SNP association tests using logistic regression analysis were done using R, assuming an additive model on a log scale consistent with previously described best-fitting genetic model for this locus (Rivera A et al., supra). Parameter estimates were evaluated by applying likelihood ratio tests. Odds ratios and 95% confidence intervals for each copy of the risk allele compared with the nonrisk wild-type genotype were obtained directly from logistic regression parameter estimates. Haplotype blocks were defined using the algorithm of Gabriel et al., (2002, Science 296: 2225-2229) implemented in Haploview 4.0 (Barrett J C et al., 2005, Bioinformatics 21:263-265). Haplotype-specific odds ratios were calculated with UNPHASED (Dudbridge F, 2003, Genet. Epidemiol. 25: 115-121; Dudbridge F, 2006, UNPHASED user guide. Technical Report 5. MRC Biostatistics Unit, Cambridge), pooling all rare haplotypes with an estimated frequency<1%.

The indel polymorphism showed highly significant association with AMD compared to controls (42.4% vs 19.3%). The odds ratio for the indel polymorphism showed a 2.9-fold increased risk of developing AMD in individuals carrying a single copy of the risk allele compared with an 8.1 fold increased risk in individuals carrying two copies of the risk allele.

Example 2

Characterization of ARMS2 Isoforms

Figure 2:
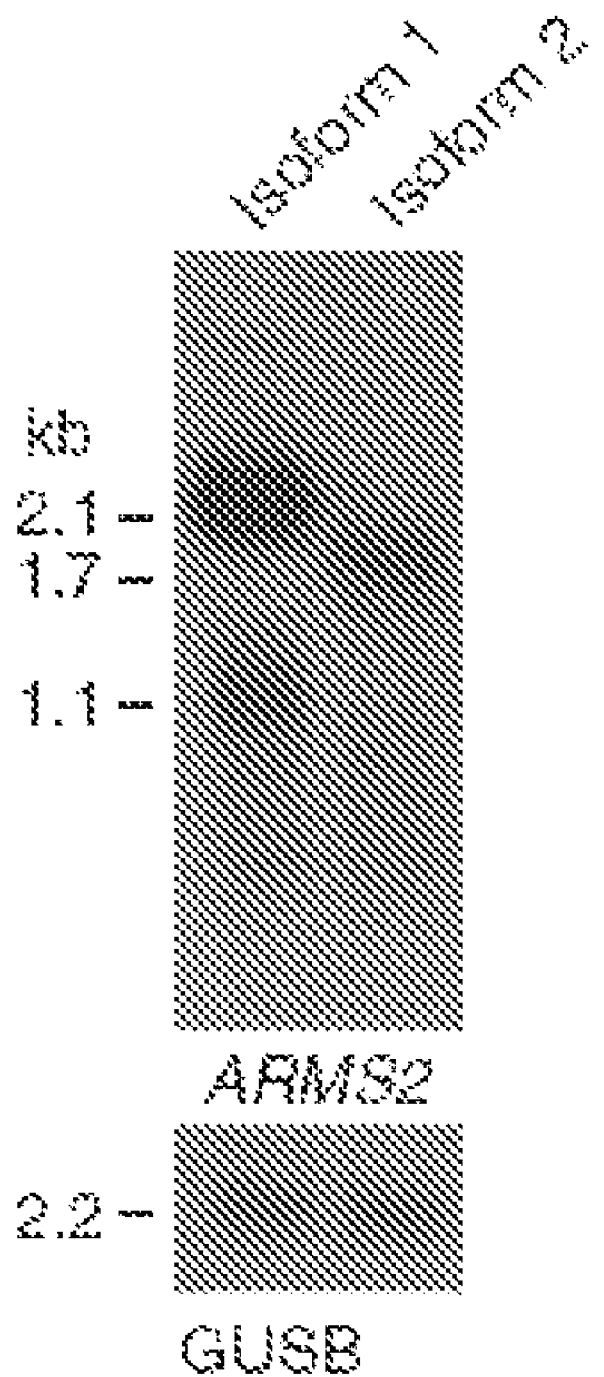
FIG. 2 shows an RNA blot of heterologously expressed ARMS2 isoforms.

The potential functional effects of the indel polymorphism on the stability of the ARMS2 transcript was analyzed. To determine major transcription initiation (TI) and functional polyadenylation sites, 5' and 3' RACE experiments were conducted. Allelic ARMS2 mRNA expression in three retinal and six placental samples in unrelated non-AMD individuals, all heterozygous at the genomic level for the indel variant and the tightly associated A69S (rs10490924) polymorphism were compared. In the samples analyzed, RT-PCR with first-strand cDNAs, either primed with oligo dT or gene-specific oligonucleotides, revealed exclusively the presence of the Ala69 allele, which is not associated with risk. To determine the sensitivity of allelic discrimination by the sequencing approach applied, dilution series of plasmid clones carrying either the Ala69 or the Ser69 variant of ARMS2 were analysed. The data demonstrates that the limits of allelic resolution by sequencing range between 1:12 to 1:13, suggesting that in the tissue samples tested, the indel ARMS2 isoform is reduced over the regular transcript by a ratio of 1:12 or less. To test the stability of the two isoforms, RNA blot analysis of heterologously expressed ARMS2 variants was conducted. Each isoform was expressed in EBNA 293 cells from its genomic locus comprising 3,749 by (nonrisk isoform) and 3,360 by (risk isoform), respectively. Strong transcription initiation (TI) site and polyadenylation signal sequences were provided by the vector construct. As shown in FIG. 2, RNA was harvested 24 h after transfection and showed a markedly reduced amount of the indel transcript (1.7 kb-isoform 2) compared to the normal variant (2.1 kb-isoform 1). Beta-glucoronidase (GUSB) served as a control for RNA integrity and equal mRNA loading.

Example 3

Expression Analysis

Figure 3:
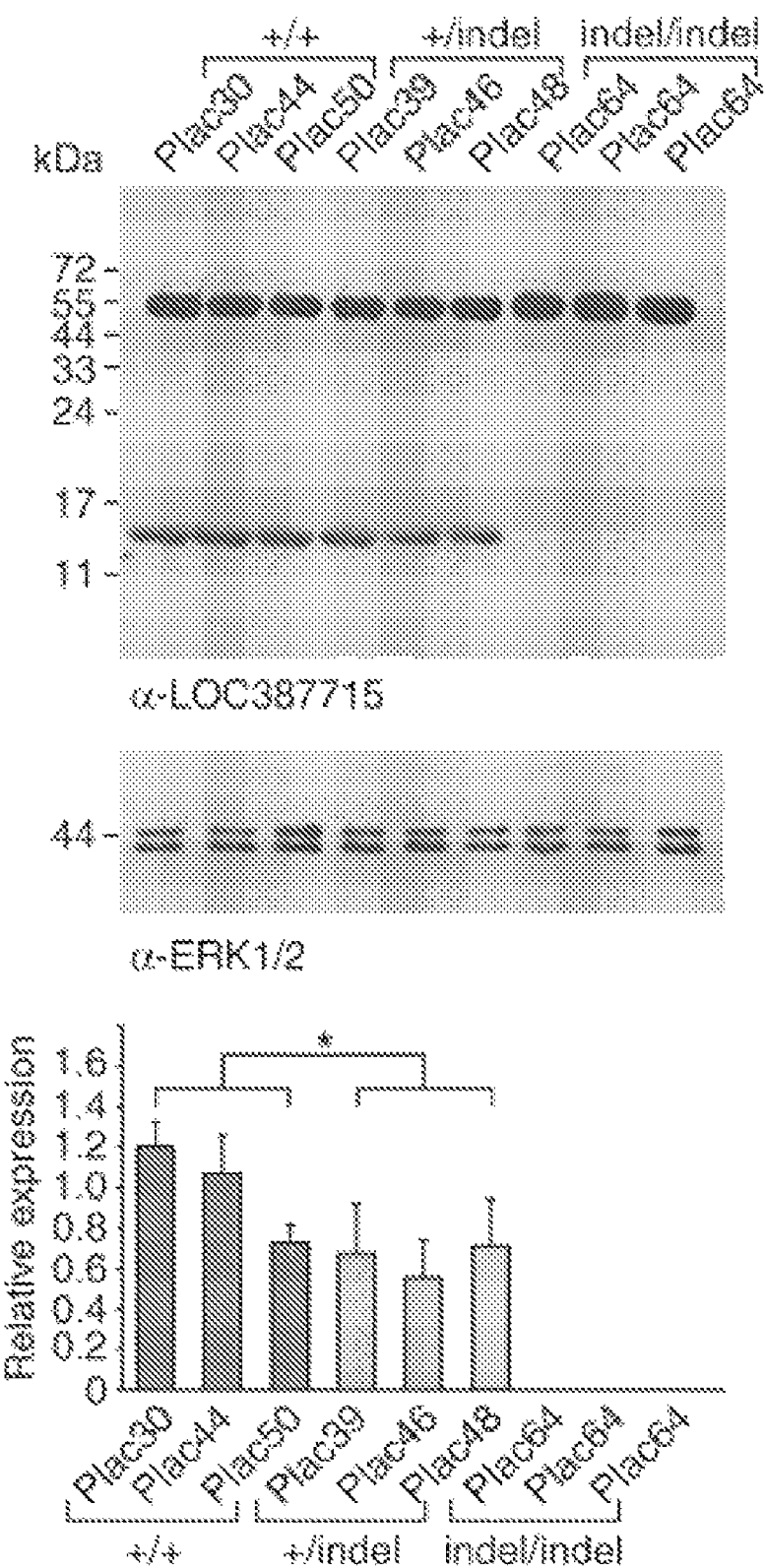
FIG. 3 shows placental ARMS2 protein expression in relation to the *372_815delins54 (indel) genotype.
Figure 4:
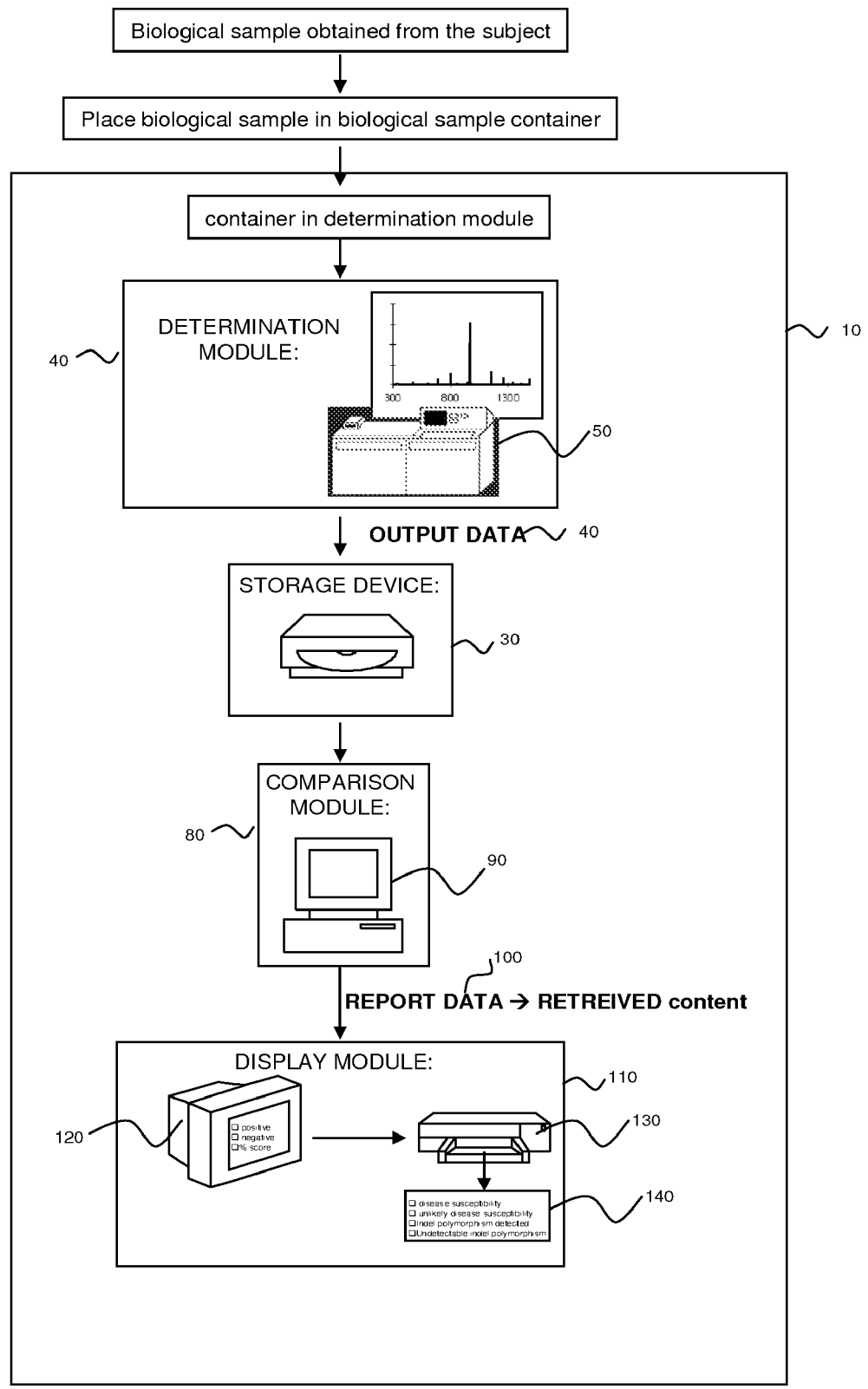
FIG. 4 shows a block diagram of a computer system according to an embodiment of the present invention.
Figure 5:
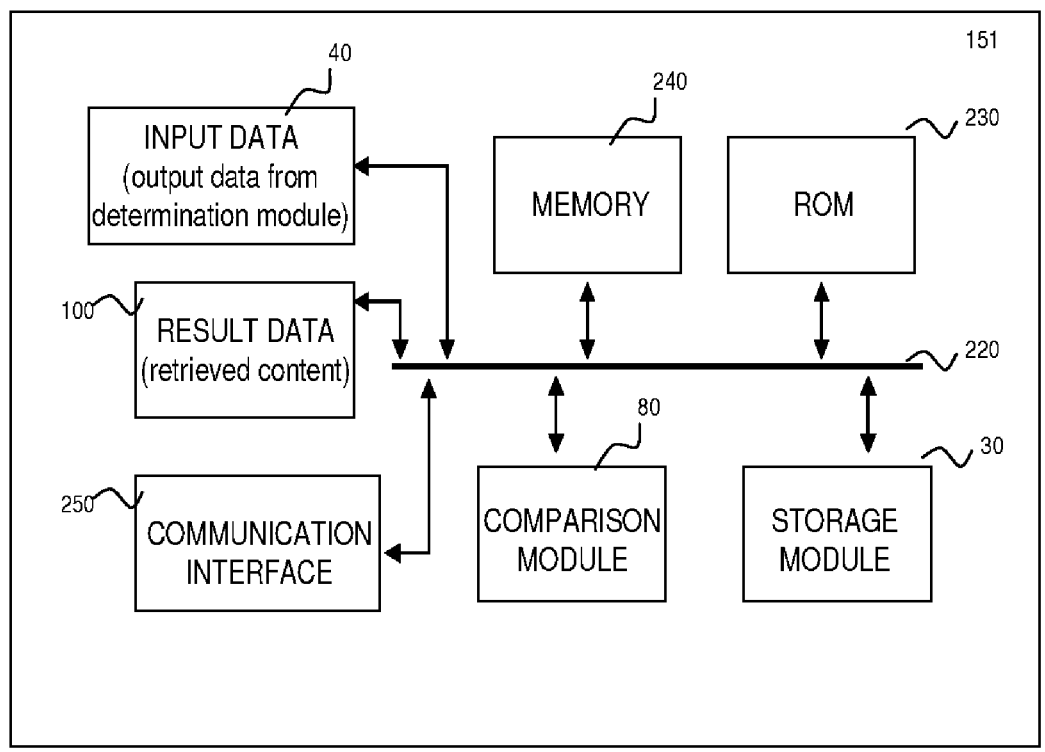
FIG. 5 shows a block diagram of a computer readable medium according to an embodiment of the present invention.

To analyze ARMS2 protein expression, rabbit polyclonal antibodies against the recombinant full-length 107 amino acid peptide were generated. Subsequent epitope mapping with a series of overlapping 15 amino acid peptides demonstrated a high specificity for the VLDPGVG (SEQ ID NO: 5) epitope of ARMS2. Protein blot analysis of immunoprecipitated ARMS2 protein from various human tissues showed a predicted protein species of approximately 13.5 kDa in placenta and, less pronounced, in retinas of several non-AMD donors. We observed weak signals in kidney, lung and heart only after overexposure of the autoradiogram (data no shown), suggesting ubiquitous expression, although with variable rates in the respective tissues. Before protein analysis, all tissues were genotyped and shown to carry exclusively ARMS2 nonrisk haplotypes (data not shown). The protein blot signals were consistent with relative expression measurements in previous mRNA expression studies. Protein expression was analysed with respect to ARMS2 genotypes. From a total of 66 randomly collected placentas, we identified 45 samples homozygous or compound heterozygous for one of the nonrisk haplotypes, as well as 20 heterozygous and 1 homozygous carrier for the unique indel risk haplotype. As shown in FIG. 3, in agreement with RT-PCR data, immunoblot analysis showed expression of the 13.5-kDa ARMS2 protein only in placentas from individuals with one or two nonrisk haplotypes. In contrast, three independent preparations from the homozygous carrier of the indel risk haplotype lacked ARMS2 protein expression. Before immunoprecipitation, supernatants of tissue homogenates were normalized to soluble extracellular signal-regulated kinase 1/2 (ERK 1/2). Signals at 50-55 kDA correspond to the immunoglobulin heavy chain. The bottom panel of FIG. 3, shows relative expression representing the mean values of three independent protein blot analyses. Asterisk indicates a double-sided P value of 0.004. Errors bars, s.e.m.

The indel polymorphism gives rise to an alternative ARMS2 isoform highly unstable at the mRNA level, consequently resulting in absence of protein expression. These findings strongly suggest that this polymorphism is the sought-after functional variant with relevance to AMD etiology.

Unless otherwise specified, all references cited are incorporated herein.

It will be understood that numerous modifications thereto will appear to those skilled in the art. Accordingly, the above description and accompanying drawings should be taken as illustrative of the invention and not in a limiting sense. It will further be understood that it is intended to cover any variations, uses, or adaptations of the invention following, in general, the principles of the invention and including such departures from the present disclosure as come within known or customary practice within the art to which the invention pertains and as may be applied to the essential features herein set forth, and as follows in the scope of the appended claims.

The invention claimed is:

1. A method for diagnosing a susceptibility to age-related macular degeneration in a human subject, the method comprising the steps of:
   amplifying a nucleic acid sequence containing position 3143 of SEQ ID NO. 1 using a first primer that binds upstream of said position and a second primer that binds downstream of said position;
   detecting an insertion/deletion polymorphism starting at position 3143 of SEQ ID NO. 1; and
   determining the genotype of the subject at position 3143 of SEQ ID NO. 1,
   wherein a homozygote for the insertion/deletion polymorphism is predictive of susceptibility to age-related macular degeneration and a heterozygote for the insertion/deletion polymorphism is predictive of a carrier for susceptibility to age-related macular degeneration wherein the insertion/deletion polymorphism comprises deletion of a nucleic acid sequence from position 3143 of SEQ ID NO: 1 to position 3585 of SEQ ID NO: 1 and insertion of a sequence from position 104 of SEQ ID NO: 2 to position 157 of SEQ ID NO: 2 in place of the deleted sequence.

2. The method of claim 1, wherein the insertion/deletion polymorphism is detected by hybridization, chemical cleavage, direct DNA sequencing, use of restriction enzymes or Southern blotting.

3. The method of claim 1, further comprising the step of obtaining a biological sample containing nucleic acid from the human subject prior to amplifying the insertion/deletion polymorphism.

* * * * *

SEQUENCE LISTING

<160> NUMBER OF SEQ ID NOS: 5

<210> SEQ ID NO 1
<211> LENGTH: 3690
<212> TYPE: DNA
<213> ORGANISM: Homo sapiens
<220> FEATURE:
<221> NAME/KEY: misc_feature
<222> LOCATION: (3143)..(3585)
<223> OTHER INFORMATION: deletion sequence

<400> SEQUENCE: 1

```
acaaaaaaac aacaaaaaat cccaaaaccc ccaaaactct cattgacccct tatctcagat      60
ttcccgaatg cttaccaccc tcgctacatc attcaagttc ttggaaacat ttaaagcatg     120
tgaaacattt aaaacattta agttggaggc tttaagttgc acgtccttta tttctaaata     180
tttcagtgtg ttttttcttaa aaaaaatttt ctcataccac agtaacatga tcaaaattgg     240
aaaatcaaca ttgattcaat actatgatct acaatcaagg tttttttttt ttttcaaatc     300
cctgggtctc tgcatttttt aaaagcttca cagatgattt caatggatac tagggacctc     360
tgttgcctcc tctggcagag caggactgag gggtggaccc tccctgagac cacccaacaa     420
ttcagggtgg agttatcagg gcgccctgac tcctggggc attttttgtgt gacgggaaaa     480
gacaatgctc ctggctgagt gagatggcag ctggcttggc aaggggacag cacctttgtc     540
accacattat gtccctgtac cctacatgct gcgcctatac ccaggaccga tggtaactga     600
ggcggagggg aaaggagggc ctgagatggc aagtctgtcc tcctcggtgg ttcctgtgtc     660
cttcatttcc actctgcgag agtctgtgct ggaccctgga gttggtggag aaggagccag     720
tgacaagcag aggagcaaac tgtctttatc acactccatg atcccagctg ctaaaatcca     780
cactgagctc tgcttaccag ccttcttctc tcctgctgga acccagagga ggttccagca     840
gcctcagcac cacctgacac tggtaagaaa tgcagatgat caggccttac cccagaccta     900
ttgaatcaga aattctggag tggtgccctg cagcttgcat tttaaccagc cttcaggtgc     960
ttctgatgca tgctcaggtt tgagcaccac tggcccacagg gaggcctagg caattcagcc    1020
ttcctctggt tgaatagctg gagaattggg aatatcagta aatacttcca atgcacctgc    1080
tacatgccag aaaaaggaaa caagaagacg cagtaggtct gagaaagtga tggggtgagc    1140
agaaacccaa agcttataga aggccatctg agtggccct caagccggtg aattggcttt    1200
agggtttact gaaggaggtg gaaacctcag cctgcttctc gtccgggttg ttagaggagt    1260
catttagaaa gctgtaccat tcttttcaata ttctcacggc tttccagtgc tcatttttcc    1320
tgctcattta tggattaaaa aaaatgcctt ggctgtatgt gtaagaaaac aacaatgcaa    1380
gtttgtagag aaagaatctg ggccttacag gtcacgttgg tttaaaattt agacatcaag    1440
cagcttagag accatgttgc caaataagct tagtaaatgc tttctaatgc ttacggaact    1500
gtggcgcttt gtgcttgcca tagtatatat aattagacaa atgagagaac acaaaggttg    1560
aaccccttcc ctctcttaat ttttgttttt tacaagcaga tttaaaattc tggctcataa    1620
tgtccttgat tcaatgttaa accatttttgc ctaaatggca gcatgttcta aatgtgagcg    1680
cgctcagctt ttcaagctgc tcccgagtga cagaaattga caagctgtca ttcaagacct    1740
ttcggtggct gcctggggct ctgtttgaat tgtatctgtc tgatactttta ccatggagag    1800
tgaaaaattt gatcacatgc catgctttta atttttctaaa gcaaatatgt tggaaggagc    1860
caattaatgc aaagatggac tgctggtctc atgcaactga tttaggggaa gggttcgcct    1920
```

```
aaattaataa aagatctgaa ttatagatct taacaaatac atagaatgta aaggcttaaa      1980
aggaaactga gcagcagcag gcctggggtt ggcttttaag tatctatatt taactaatag      2040
acatgaatgt tttgatttga tattagaaat gctagtgctg gagtctctga gcctactctg      2100
gctcgagagg atgccctatc taaaaaacaa aaacaaaaa  aaaaaagaa  aaagaaaaa       2160 aagaaatgct ggtattgtaa ttctaaagtg cttcagaaat tctcaaaaat aggccaggca      2220
tggtggctca tggctgtata ccagcacttt gggaggccaa ggtgggcaaa tcacttgcag      2280
tcaggagttt gagaccagcc tggtcaacat ggtgaaaccc catctctact aaaaatacag      2340
aaattagcca ggcatggtgg cagcacctgt aatcccagct acttgggagg ctgaggcagg      2400
agaatcgcta gaacctggga ggtggaggtt gcagtgagcc aagaccgcac cactgcactc      2460
cagcctgggc aacagagtga gactctatct caaaaaaaaa aaaaaaagt  tctcaaaagt      2520 attttgaact tcctcacctt tgtcctattt tggaaggagg gggtctacat tgaagagatc      2580
atacagaaat aaattaattg ttacaaaagg aatggaatgt ctatacttct taccctattg      2640
agttacatta actgcatctt caacttaatt taaagtgctc ctcaacctaa aatatcgtca      2700
tgtgtcttta aaaatgcata ttactaaatc tatttttttt tcagtctatc atccacactg      2760
cagcaaggtg attctgccaa aacatatctc cttaaaagcc aactggagct tctcatcagc      2820
atcaatgtga agccaaaaat ccttaggagg acagagggag tccctcacaa cctagactgg      2880
tccccttccc tccagctgcc tcaactgtcc acaggactct cttcccacct gcggccacac      2940
tgtgcaacct ggaatttccc cacctgggcg gactcatcac gtcatcacca attggatgca      3000
tcttctgctc tgtgcagctg gtgaaatctt tctcaaccct tgagatgcag cccaatcttc      3060
tcctaacatc tggattcctc tctgtcactg cattccctcc tgtcatcctg cctttgtttt      3120
cttgccctcc tttctctccc gggtgatagg cattaactaa aattaaataa aaattcagat      3180
catccttgca cttgctgcat ttcaaatgct tggcagtcac atgtagttag tggctaccct      3240
cttggacagc acagatagag attatttcca tcactgcaga aaattctaga ctttgagctt      3300
cttgaggaca ggggcttgat cattcgacac tgctttacag tgtctagcag tgtctaccct      3360
gtggcagggg ctcaggaaat ttttcctgaa ccgaacctaa ctgaactgat gtgggtttgt      3420
catcagggtg tacctgctgt taaaggaggt tacgacctct gatgctgggg tggccagagg      3480
ggatgggagt gggtctggca ctctgaggaa agggggtgaa accagctgag aagtcatctt      3540
ttacctgctg gcatggcccc agccaggggtt ctgttgctat gggagaatgg gtgagtaggg     3600
atggattaca ccaccctgga tctagaggac aacctggctt gaggggcatg ggggacgctg      3660
gaagtcaggg taagaagctt ggacttcatt                                       3690
```

<210> SEQ ID NO 2
<211> LENGTH: 415
<212> TYPE: DNA
<213> ORGANISM: Homo sapiens
<220> FEATURE:
<221> NAME/KEY: misc_feature
<222> LOCATION: (104)..(157)
<223> OTHER INFORMATION: insertion

<400> SEQUENCE: 2

```
ttgagatgca gcccaatctt ctcctaacat ctggattcct ctctgtcact gcattccctc       60
ctgtcatcct gcctttgttt tcttgccctc ctttctctcc cggttattaa ttaattaact      120
aaaattaaat tatttagtta atttaattaa ctaaactaat gggtgagtag ggatggatta      180
caccaccctg gatctagagg acaacctggc ttgaggggca tggggacgc  tggaagtcag      240
```

```
ggtaagaagc ttggacttca ttctactggc atggagagcc cctggaaact actgagcagt    300
agagggatag gctaagctta taggaggagc caaaattatt actgtagctc cttagatctt    360
agatcctgtg acttaggaaa ggcaatagga gcccctgagc attctgggtc ctttg         415

<210> SEQ ID NO 3
<211> LENGTH: 443
<212> TYPE: DNA
<213> ORGANISM: Homo sapiens

<400> SEQUENCE: 3
gtgataggca ttaactaaaa ttaaataaaa attcagatca tccttgcact tgctgcattt     60
caaatgcttg gcagtcacat gtagttagtg gctaccctct tggacagcac agatagagat    120
tatttccatc actgcagaaa attctagact ttgagcttct tgaggacagg ggcttgatca    180
ttcgacactg ctttacagtg tctagcagtg tctaccctgt ggcaggggct caggaaattt    240
ttcctgaacc gaacctaact gaactgatgt gggtttgtca tcagggtgta cctgctgtta    300
aaggaggtta cgacctctga tgctggggtg gccagagggg atgggagtgg gtctggcact    360
ctgaggaaag ggggtgaaac cagctgagaa gtcatctttt acctgctggc atggccccag    420
ccagggttct gttgctatgg gag                                            443

<210> SEQ ID NO 4
<211> LENGTH: 57
<212> TYPE: DNA
<213> ORGANISM: Homo sapiens

<400> SEQUENCE: 4
cggttattaa ttaattaact aaaattaaat tatttagtta atttaattaa ctaaact        57

<210> SEQ ID NO 5
<211> LENGTH: 7
<212> TYPE: PRT
<213> ORGANISM: Homo sapiens

<400> SEQUENCE: 5

Val Leu Asp Pro Gly Val Gly
1               5
```